US008376865B2

(12) United States Patent
Forster et al.

(10) Patent No.: US 8,376,865 B2
(45) Date of Patent: Feb. 19, 2013

(54) TORQUE SHAFT AND TORQUE SHAFT DRIVE

(75) Inventors: David C. Forster, Los Altos Hills, CA (US); Brian Beckey, Woodside, CA (US); Brandon Walsh, Syracuse, UT (US); Scott Heneveld, Whitmore, CA (US); Alex T. Roth, Redwood City, CA (US)

(73) Assignee: CardiacMD, Inc., Los Altos, CA (US)

( * ) Notice: Subject to any disclaimer, the term of this patent is extended or adjusted under 35 U.S.C. 154(b) by 412 days.

(21) Appl. No.: 12/305,620

(22) PCT Filed: Jun. 19, 2007

(86) PCT No.: PCT/US2007/071535
§ 371 (c)(1),
(2), (4) Date: Dec. 18, 2008

(87) PCT Pub. No.: WO2007/149841
PCT Pub. Date: Dec. 27, 2007

(65) Prior Publication Data
US 2009/0182416 A1   Jul. 16, 2009

Related U.S. Application Data

(60) Provisional application No. 60/805,334, filed on Jun. 20, 2006.

(51) Int. Cl.
*F16D 3/50* (2006.01)
(52) U.S. Cl. .......................................... 464/78; 464/149
(58) Field of Classification Search .................... 464/51, 464/78–80, 149, 157
See application file for complete search history.

(56) References Cited

U.S. PATENT DOCUMENTS

| 376,581 | A | | 1/1888 | Byrnes |
| 1,008,317 | A | * | 11/1911 | Fink ............................... 464/157 |
| 1,314,601 | A | | 9/1919 | McCaskey |
| 2,515,365 | A | | 7/1950 | Zublin |
| 3,579,642 | A | | 5/1971 | Hefferman |
| 3,583,393 | A | | 6/1971 | Takahashi |
| 3,587,115 | A | | 6/1971 | Shiley |
| 3,657,744 | A | | 4/1972 | Ersek |
| 3,671,979 | A | | 6/1972 | Moulopoulos |
| 3,755,823 | A | | 9/1973 | Hancock |
| 4,056,854 | A | | 11/1977 | Boretos et al. |
| 4,106,129 | A | | 8/1978 | Carpentier et al. |

(Continued)

FOREIGN PATENT DOCUMENTS

| DE | 384909 C | 12/1923 |
| EP | 0626604 | 11/1994 |

(Continued)

OTHER PUBLICATIONS

U.S. Appl. No. 11/066,126—Office Action, Dec. 22, 2009.

(Continued)

*Primary Examiner* — Gregory Binda
(74) *Attorney, Agent, or Firm* — Dickstein Shapiro LLP; Mark A. Stirrat (57) ABSTRACT

Torque shafts and other related systems and methods are described herein. The torque shafts are both flexible and capable of transmitting torque. The torque shafts are useful for procedures that require torque and pushability to drive or deploy a device. The flexibility and pushability of the torque shafts enable them to curve along a tortuous path, and the torque transferring capability of the shafts enable them to transmit torque along the shaft.

2 Claims, 11 Drawing Sheets

U.S. PATENT DOCUMENTS

| | | |
|---|---|---|
| 4,108,211 A | 8/1978 | Tanaka |
| 4,328,839 A | 5/1982 | Lyons et al. |
| 4,339,831 A | 7/1982 | Johnson |
| 4,340,091 A | 7/1982 | Skelton et al. |
| 4,362,520 A | 12/1982 | Perry |
| 4,624,822 A | 11/1986 | Arru et al. |
| 4,683,883 A | 8/1987 | Martin |
| 4,692,165 A | 9/1987 | Bokros |
| 4,758,151 A | 7/1988 | Arru et al. |
| 4,822,345 A | 4/1989 | Danforth |
| 4,822,353 A | 4/1989 | Bokros |
| 4,834,069 A | 5/1989 | Umeda |
| 4,856,516 A | 8/1989 | Hillstead |
| 4,878,495 A | 11/1989 | Grayzel |
| 4,878,906 A | 11/1989 | Lindemann et al. |
| 4,960,424 A | 10/1990 | Grooters |
| 4,994,077 A | 2/1991 | Dobben |
| 5,002,567 A | 3/1991 | Bona et al. |
| 5,037,434 A | 8/1991 | Lane |
| 5,078,737 A | 1/1992 | Bona et al. |
| 5,098,374 A | 3/1992 | Othel-Jacobsen et al. |
| 5,123,919 A | 6/1992 | Sauter et al. |
| 5,163,953 A | 11/1992 | Vince |
| 5,163,954 A | 11/1992 | Curcio et al. |
| 5,178,129 A | 1/1993 | Chikama et al. |
| 5,213,580 A | 5/1993 | Slepian et al. |
| 5,238,454 A | 8/1993 | Schmidt |
| 5,238,565 A | 8/1993 | Schmidt |
| 5,271,382 A | 12/1993 | Chikama |
| 5,312,427 A | 5/1994 | Shturman |
| 5,325,845 A | 7/1994 | Adair |
| 5,326,371 A | 7/1994 | Love et al. |
| 5,328,471 A | 7/1994 | Slepian |
| 5,370,685 A | 12/1994 | Stevens |
| 5,397,348 A | 3/1995 | Campbell et al. |
| 5,397,351 A | 3/1995 | Pavcnik et al. |
| 5,403,305 A | 4/1995 | Sauter et al. |
| 5,411,552 A | 5/1995 | Andersen et al. |
| 5,423,886 A | 6/1995 | Arru et al. |
| 5,443,474 A | 8/1995 | Sfakianos et al. |
| 5,454,838 A | 10/1995 | Vallana et al. |
| 5,522,885 A | 6/1996 | Love et al. |
| 5,531,094 A | 7/1996 | More et al. |
| 5,545,214 A | 8/1996 | Stevens |
| 5,554,185 A | 9/1996 | Block et al. |
| 5,560,487 A | 10/1996 | Starr |
| 5,582,607 A | 12/1996 | Lackman |
| 5,607,442 A | 3/1997 | Fischell et al. |
| 5,620,456 A | 4/1997 | Sauer et al. |
| 5,668,425 A | 9/1997 | Marioni et al. |
| 5,695,515 A | 12/1997 | Orejola |
| 5,713,860 A | 2/1998 | Kaplan et al. |
| 5,713,953 A | 2/1998 | Vallana et al. |
| 5,716,370 A | 2/1998 | Williamson et al. |
| 5,724,705 A | 3/1998 | Hauser et al. |
| 5,755,731 A | 5/1998 | Grinberg |
| 5,772,578 A | 6/1998 | Heimberger et al. |
| 5,772,672 A | 6/1998 | Toy et al. |
| 5,807,241 A | 9/1998 | Heimberger |
| 5,814,097 A | 9/1998 | Sterman et al. |
| 5,816,923 A | 10/1998 | Milo et al. |
| 5,823,342 A | 10/1998 | Caudillo et al. |
| 5,840,081 A | 11/1998 | Andersen et al. |
| 5,855,601 A | 1/1999 | Bessler et al. |
| 5,868,708 A | 2/1999 | Hart et al. |
| 5,891,195 A | 4/1999 | Klostermeyer et al. |
| 5,919,225 A | 7/1999 | Lau et al. |
| 5,921,993 A | 7/1999 | Yoon |
| 5,925,063 A | 7/1999 | Khosravi |
| 5,928,136 A | 7/1999 | Barry |
| 5,957,949 A | 9/1999 | Leonhardt et al. |
| 5,980,570 A | 11/1999 | Simpson |
| 5,984,959 A | 11/1999 | Robertson et al. |
| 6,027,779 A | 2/2000 | Campbell et al. |
| 6,042,607 A | 3/2000 | Williamson, IV et al. |
| 6,051,014 A | 4/2000 | Jang |
| 6,053,922 A | 4/2000 | Krause et al. |
| 6,090,138 A | 7/2000 | Chasak et al. |
| 6,092,529 A | 7/2000 | Cox |
| 6,093,530 A | 7/2000 | McIlroy et al. |
| 6,102,944 A | 8/2000 | Huynh et al. |
| 6,102,945 A | 8/2000 | Campbell |
| 6,117,169 A | 9/2000 | Moe |
| 6,132,986 A | 10/2000 | Pathak et al. |
| 6,143,024 A | 11/2000 | Campbell et al. |
| 6,143,025 A | 11/2000 | Stobie et al. |
| 6,162,172 A | 12/2000 | Cosgrove et al. |
| 6,168,614 B1 | 1/2001 | Andersen et al. |
| 6,174,331 B1 | 1/2001 | Moe et al. |
| 6,182,664 B1 | 2/2001 | Cosgrove |
| 6,197,053 B1 | 3/2001 | Cosgrove et al. |
| 6,199,696 B1 | 3/2001 | Lytle et al. |
| 6,206,918 B1 | 3/2001 | Campbell et al. |
| 6,217,610 B1 | 4/2001 | Carpentier et al. |
| 6,231,578 B1 | 5/2001 | Rajhansa |
| 6,231,602 B1 | 5/2001 | Carpentier et al. |
| 6,241,765 B1 | 6/2001 | Griffin et al. |
| 6,245,102 B1 | 6/2001 | Jayaraman |
| 6,270,526 B1 | 8/2001 | Cox |
| 6,283,995 B1 | 9/2001 | Moe et al. |
| 6,287,339 B1 | 9/2001 | Vazquez et al. |
| 6,299,637 B1 | 10/2001 | Shaolian et al. |
| 6,299,638 B1 | 10/2001 | Sauter |
| 6,338,740 B1 | 1/2002 | Carpentier |
| 6,342,070 B1 | 1/2002 | Nguyen-Thien-Nhon |
| 6,348,068 B1 | 2/2002 | Campbell et al. |
| 6,350,281 B1 | 2/2002 | Rhee |
| 6,350,732 B1 | 2/2002 | Moore et al. |
| 6,364,905 B1 | 4/2002 | Simpson et al. |
| 6,371,983 B1 | 4/2002 | Lane |
| 6,383,147 B1 | 5/2002 | Stobie |
| 6,391,054 B2 | 5/2002 | Carpentier et al. |
| 6,402,780 B2 | 6/2002 | Williamson, IV et al. |
| 6,405,084 B2 | 6/2002 | Plicchi et al. |
| 6,409,758 B2 | 6/2002 | Stobie et al. |
| 6,425,916 B1 | 7/2002 | Garrison et al. |
| 6,453,062 B1 | 9/2002 | MacNutt et al. |
| 6,454,799 B1 | 9/2002 | Schreck |
| 6,458,155 B1 | 10/2002 | Van Nguyen et al. |
| 6,461,382 B1 | 10/2002 | Cao |
| 6,475,239 B1 | 11/2002 | Campbell et al. |
| 6,479,079 B1 | 11/2002 | Pathak et al. |
| 6,482,228 B1 | 11/2002 | Norred |
| 6,485,512 B1 | 11/2002 | Cheng |
| 6,493,585 B2 | 12/2002 | Plicchi et al. |
| 6,530,952 B2 | 3/2003 | Vesely |
| 6,544,279 B1 | 4/2003 | Hopkins et al. |
| 6,558,418 B2 | 5/2003 | Carpentier et al. |
| 6,565,602 B2 | 5/2003 | Rolando et al. |
| 6,569,196 B1 | 5/2003 | Vesely |
| 6,572,642 B2 | 6/2003 | Rinaldi et al. |
| 6,582,462 B1 | 6/2003 | Andersen et al. |
| 6,585,632 B2 | 7/2003 | Vallana et al. |
| 6,585,766 B1 | 7/2003 | Huynh et al. |
| 6,596,471 B2 | 7/2003 | Pathak et al. |
| 6,602,262 B2 | 8/2003 | Griego et al. |
| 6,602,288 B1 | 8/2003 | Cosgrove et al. |
| 6,613,085 B1 | 9/2003 | Anderson et al. |
| 6,616,690 B2 | 9/2003 | Rolando et al. |
| 6,635,085 B1 | 10/2003 | Caffey et al. |
| 6,638,303 B1 | 10/2003 | Campbell |
| 6,652,578 B2 | 11/2003 | Bailey et al. |
| 6,663,667 B2 | 12/2003 | Dehdashtian et al. |
| 6,673,109 B2 | 1/2004 | Cox |
| 6,679,871 B2 | 1/2004 | Hahnen |
| 6,682,493 B2 | 1/2004 | Mirigian |
| 6,682,543 B2 | 1/2004 | Barbut et al. |
| 6,682,558 B2 | 1/2004 | Tu et al. |
| 6,682,559 B2 | 1/2004 | Myers et al. |
| 6,689,149 B2 | 2/2004 | Maahs |
| 6,692,512 B2 | 2/2004 | Jang |
| 6,706,033 B1 | 3/2004 | Martinez et al. |
| 6,719,787 B2 | 4/2004 | Cox |
| 6,719,788 B2 | 4/2004 | Cox |
| 6,719,789 B2 | 4/2004 | Cox |
| 6,723,122 B2 | 4/2004 | Yang et al. |
| 6,730,118 B2 | 5/2004 | Spenser et al. |

| | | | | | | |
|---|---|---|---|---|---|---|
| 6,733,513 B2 | 5/2004 | Boyle et al. | | 2004/0015224 A1 | 1/2004 | Armstrong et al. |
| 6,733,525 B2 | 5/2004 | Yang et al. | | 2004/0030382 A1 | 2/2004 | St. Goar et al. |
| 6,736,845 B2 | 5/2004 | Marquez et al. | | 2004/0034380 A1 | 2/2004 | Woolfson et al. |
| 6,736,846 B2 | 5/2004 | Cox | | 2004/0049266 A1 | 3/2004 | Anduiza et al. |
| 6,743,239 B1 | 6/2004 | Kuehn et al. | | 2004/0078074 A1 | 4/2004 | Anderson et al. |
| 6,767,362 B2 | 7/2004 | Schreck | | 2004/0092858 A1 | 5/2004 | Wilson et al. |
| 6,770,083 B2 | 8/2004 | Seguin | | 2004/0092989 A1 | 5/2004 | Wilson et al. |
| 6,783,988 B1 | 8/2004 | Dinh et al. | | 2004/0093060 A1 | 5/2004 | Seguin et al. |
| 6,790,219 B1 | 9/2004 | Murphy | | 2004/0093080 A1 | 5/2004 | Helmus et al. |
| 6,796,972 B1 | 9/2004 | Sinofsky et al. | | 2004/0127979 A1 | 7/2004 | Wilson et al. |
| 6,797,000 B2 | 9/2004 | Simpson et al. | | 2004/0148017 A1 | 7/2004 | Stobie |
| 6,805,710 B2 | 10/2004 | Bolling et al. | | 2004/0148018 A1 | 7/2004 | Carpentier et al. |
| 6,821,279 B2 | 11/2004 | Di Emidio | | 2004/0153140 A1 | 8/2004 | Rolando et al. |
| 6,821,297 B2 | 11/2004 | Snyders | | 2004/0158276 A1 | 8/2004 | Barbut et al. |
| 6,842,649 B2 | 1/2005 | Laabs et al. | | 2004/0172124 A1 | 9/2004 | Vallana et al. |
| 6,846,324 B2 | 1/2005 | Stobie | | 2004/0186563 A1 | 9/2004 | Lobbi |
| 6,849,088 B2 | 2/2005 | Dehdashtian et al. | | 2004/0199245 A1 | 10/2004 | Lauterjung |
| 6,858,039 B2 | 2/2005 | McCarthy | | 2004/0210304 A1 | 10/2004 | Seguin et al. |
| 6,875,231 B2 | 4/2005 | Anduiza et al. | | 2004/0225352 A1 | 11/2004 | Osborne et al. |
| 6,878,168 B2 | 4/2005 | Carpentier et al. | | 2004/0243222 A1 | 12/2004 | Osborne et al. |
| 6,893,460 B2 | 5/2005 | Spenser et al. | | 2004/0249433 A1 | 12/2004 | Freitag |
| 6,896,698 B2 | 5/2005 | Rolando et al. | | 2005/0027337 A1 | 2/2005 | Rudko et al. |
| 6,908,481 B2 | 6/2005 | Cribier | | 2005/0033398 A1 | 2/2005 | Seguin |
| 6,921,397 B2 | 7/2005 | Corcoran et al. | | 2005/0038497 A1 | 2/2005 | Neuendorf et al. |
| 6,939,365 B1 | 9/2005 | Fogarty et al. | | 2005/0043760 A1 | 2/2005 | Fogarty et al. |
| 6,945,997 B2 | 9/2005 | Huynh et al. | | 2005/0043790 A1 | 2/2005 | Seguin |
| 6,949,101 B2 | 9/2005 | McCleary et al. | | 2005/0043792 A1 | 2/2005 | Solem et al. |
| 6,951,571 B1 | 10/2005 | Srivastava | | 2005/0065594 A1 | 3/2005 | DiMatteo et al. |
| 6,962,605 B2 | 11/2005 | Cosgrove et al. | | 2005/0075584 A1 | 4/2005 | Cali |
| 6,986,775 B2 | 1/2006 | Morales et al. | | 2005/0075712 A1 | 4/2005 | Biancucci et al. |
| 6,988,881 B2 | 1/2006 | Motsenbocker et al. | | 2005/0075725 A1 | 4/2005 | Rowe |
| 6,989,028 B2 | 1/2006 | Lashinski et al. | | 2005/0090888 A1 | 4/2005 | Hines et al. |
| 7,004,176 B2 | 2/2006 | Lau | | 2005/0096734 A1 | 5/2005 | Majercak et al. |
| 7,011,669 B2 | 3/2006 | Kimblad | | 2005/0096740 A1 | 5/2005 | Langberg et al. |
| 7,011,681 B2 | 3/2006 | Vesely | | 2005/0113640 A1 | 5/2005 | Saadat et al. |
| 7,011,682 B2 | 3/2006 | Lashinski et al. | | 2005/0137686 A1 | 6/2005 | Salahieh et al. |
| 7,014,648 B2 | 3/2006 | Ambrisco et al. | | 2005/0137687 A1 | 6/2005 | Salahieh et al. |
| 7,018,406 B2 | 3/2006 | Seguin et al. | | 2005/0137688 A1 | 6/2005 | Salahieh et al. |
| 7,060,092 B2 | 6/2006 | Kuribayashi et al. | | 2005/0137689 A1 | 6/2005 | Salahieh et al. |
| 7,090,637 B2 | 8/2006 | Danitz et al. | | 2005/0137690 A1 | 6/2005 | Salahieh et al. |
| 7,250,027 B2 | 7/2007 | Barry | | 2005/0137691 A1 | 6/2005 | Salahieh et al. |
| 7,252,682 B2 | 8/2007 | Seguin | | 2005/0137695 A1 | 6/2005 | Salahieh et al. |
| 7,374,571 B2 | 5/2008 | Pease et al. | | 2005/0137696 A1 | 6/2005 | Salahieh et al. |
| 7,413,543 B2 | 8/2008 | Banik et al. | | 2005/0137699 A1 | 6/2005 | Salahieh et al. |
| 2001/0016758 A1 | 8/2001 | Plicchi et al. | | 2005/0137701 A1 | 6/2005 | Salahieh et al. |
| 2001/0018600 A1 | 8/2001 | Plicchi et al. | | 2005/0143809 A1 | 6/2005 | Salahieh et al. |
| 2001/0039450 A1 | 11/2001 | Pavcnik et al. | | 2005/0187616 A1 | 8/2005 | Realyvasquez |
| 2001/0049541 A1 | 12/2001 | Plicchi et al. | | 2005/0197695 A1 | 9/2005 | Stacchino et al. |
| 2002/0032482 A1 | 3/2002 | Cox | | 2005/0203614 A1 | 9/2005 | Forster et al. |
| 2002/0038128 A1 | 3/2002 | Turovkiy et al. | | 2005/0203615 A1 | 9/2005 | Forster et al. |
| 2002/0042651 A1 | 4/2002 | Liddicoat et al. | | 2005/0203617 A1 | 9/2005 | Forster et al. |
| 2002/0052647 A1 | 5/2002 | Rolando et al. | | 2005/0228485 A1 | 10/2005 | Rolando et al. |
| 2002/0055775 A1 | 5/2002 | Carpentier et al. | | 2005/0228495 A1 | 10/2005 | Macoviak |
| 2002/0058994 A1 | 5/2002 | Hill et al. | | 2005/0267493 A1 | 12/2005 | Schreck et al. |
| 2002/0072793 A1 | 6/2002 | Rolando et al. | | 2005/0277959 A1 | 12/2005 | Cosgrove et al. |
| 2002/0095173 A1 | 7/2002 | Mazzocchi et al. | | 2006/0004442 A1 | 1/2006 | Spenser et al. |
| 2002/0099441 A1 | 7/2002 | Dehdashtian | | 2006/0015179 A1 | 1/2006 | Bulman-Fleming et al. |
| 2002/0117264 A1 | 8/2002 | Rinaldi et al. | | 2006/0025787 A1 | 2/2006 | Morales et al. |
| 2002/0133226 A1 | 9/2002 | Marquez et al. | | 2006/0025854 A1 | 2/2006 | Lashinski et al. |
| 2002/0138138 A1 | 9/2002 | Yang | | 2006/0025855 A1 | 2/2006 | Lashinski et al. |
| 2002/0161431 A1 | 10/2002 | Stobie et al. | | 2006/0052867 A1 | 3/2006 | Revuelta et al. |
| 2002/0163104 A1 | 11/2002 | Motsenbocker et al. | | 2006/0058871 A1 | 3/2006 | Zakay et al. |
| 2002/0183766 A1 | 12/2002 | Seguin | | 2006/0069424 A1 | 3/2006 | Acosta et al. |
| 2002/0183831 A1 | 12/2002 | Rolando et al. | | 2006/0095052 A1 | 5/2006 | Chambers |
| 2003/0009076 A1 | 1/2003 | Vallana et al. | | 2006/0122633 A1 | 6/2006 | To et al. |
| 2003/0023262 A1 | 1/2003 | Welch | | 2006/0173537 A1 | 8/2006 | Yang et al. |
| 2003/0027332 A1 | 2/2003 | Lafrance et al. | | 2006/0217764 A1 | 9/2006 | Abbott et al. |
| 2003/0033002 A1 | 2/2003 | Dehdashtian et al. | | 2006/0281566 A1 | 12/2006 | Lee |
| 2003/0036795 A1 | 2/2003 | Andersen et al. | | 2007/0016286 A1 | 1/2007 | Herrmann et al. |
| 2003/0050694 A1 | 3/2003 | Yang et al. | | 2007/0049800 A1 | 3/2007 | Boulais |
| 2003/0055495 A1 | 3/2003 | Pease et al. | | 2007/0088431 A1 | 4/2007 | Bourang et al. |
| 2003/0065356 A1 | 4/2003 | Tsugita et al. | | 2007/0167679 A1 | 7/2007 | Miyamoto et al. |
| 2003/0114913 A1 | 6/2003 | Spenser et al. | | 2008/0051802 A1 | 2/2008 | Schostek et al. |
| 2003/0114917 A1 | 6/2003 | Holloway et al. | | 2008/0140172 A1 | 6/2008 | Carpenter et al. |
| 2003/0130721 A1 | 7/2003 | Martin et al. | | | | |
| 2003/0153943 A1 | 8/2003 | Michael et al. | | | FOREIGN PATENT DOCUMENTS | |
| 2003/0153946 A1 | 8/2003 | Kimblad | | EP | 1235000 A1 | 8/2002 |
| 2003/0195613 A1 | 10/2003 | Curcio et al. | | EP | 1933726 A2 | 6/2008 |
| 2003/0212433 A1 | 11/2003 | Ambrisco et al. | | FR | 359554 A | 3/1906 |

| | | |
|---|---|---|
| FR | 507937 A | 9/1920 |
| FR | 2634260 | 7/1989 |
| GB | 621884 | 4/1949 |
| JP | 5184525 | 7/1993 |
| WO | WO 91/17720 | 11/1991 |
| WO | 97/35482 | 10/1997 |
| WO | WO 99/33414 | 7/1999 |
| WO | WO 01/76510 A2 | 10/2001 |
| WO | 03/008818 A1 | 1/2003 |
| WO | WO 03/003949 A2 | 1/2003 |
| WO | WO 03/047468 A1 | 6/2003 |
| WO | WO 03/096932 A1 | 11/2003 |
| WO | WO 03/105670 A2 | 12/2003 |
| WO | 2004/103430 A2 | 12/2004 |
| WO | WO 2005009285 A2 | 2/2005 |
| WO | WO 2005/076973 A2 | 8/2005 |
| WO | WO 2005/087140 A1 | 9/2005 |
| WO | WO 2006/066150 A2 | 6/2006 |

OTHER PUBLICATIONS

U.S. Appl. No. 11/066,126—Office Action, Oct. 16, 2008.
U.S. Appl. No. 11/066,126—Office Action, Apr. 3, 2009.
U.S. Appl. No. 11/066,124—Office Action, Mar. 7, 2007.
U.S. Appl. No. 11/066,124—Office Action, Mar. 7, 2008.
U.S. Appl. No. 11/066,124—Office Action, Oct. 2, 2008.
U.S. Appl. No. 11/066,124—Office Action, Jun. 9, 2009.
U.S. Appl. No. 11/067,330—Office Action, Apr. 16, 2007.
U.S. Appl. No. 11/067,330—Office Action, Jun. 11, 2008.
U.S. Appl. No. 11/067,330—Office Action, Jun. 10, 2009.
U.S. Appl. No. 11/364,715—Office Action, Dec. 11, 2006.
U.S. Appl. No. 11/364,715—Office Action, Oct. 18, 2007.
U.S. Appl. No. 11/364,715—Office Action, Jan. 12, 2009.
CN Ser. No. 200580012735.5—Office Action, Jan. 9, 2009.
CN Ser. No. 200580012735.5—Office Action, Jul. 10, 2009.
EP Ser. No. 05723873.5—ESR, Nov. 3, 2009.
WO Ser. No. WO2007/101159—ISR, Apr. 24, 2008.
WO Ser. No. WO2007/101160—ISR, Dec. 11, 2007.
WO Ser. No. WO2007/149905—ISR, Aug. 29, 2008.
WO Ser. No. WO2007/149841—ISR, Jul. 30, 2008.
WO Ser. No. WO2007/149933—ISR, Aug. 15, 2008.
WO Ser. No. WO2007/149910—ISR, Jan. 28, 2008.
WO Ser. No. WO2008/030946—ISR, Jan. 11, 2008.
European Search Report, Appln. No. 07798835.0-2320, Mar. 2, 2010.
European Search Report, Appln. No. 07814708.9-2320. Mar. 3, 2010.
European Search Report, Appl. No. 07798811.2-2320, Mar. 8, 2010.
European Search Report, Appl. No. 07757493.7-2320, Mar. 15, 2010.

* cited by examiner

TORQUE SHAFT AND TORQUE SHAFT DRIVE

CROSS-REFERENCE TO RELATED APPLICATIONS

This application claim is a national stage entry under 35 U.S.C. section 371 of PCT Application Serial No. PCT/US2007/071535, filed Jun. 19, 2007, which claims priority to U.S. Provisional Application Ser. No. 60/805,334, filed Jun. 20, 2006.

BACKGROUND OF THE INVENTION

Typical flexible shafts are susceptible to torque to the extent that rotation of one side of the shaft does not correlate to rotation of the opposite side of the shaft. For instance, in applications where a shaft is used to transmit torque along a tortuous path to a remote device, it is desirable to maintain a correlation between rotation on one side of the shaft to rotation at the remote device such that the amount of rotation at the remote device can be tracked with certainty. Typical shafts are susceptible to buckling, kinking or require an excessive amount of initial rotation at the outset before correlatable torque transmission occurs. Accordingly, there is a need for a flexible shaft that transmits torque with improved certainty, adequacy and/or efficiency.

BRIEF SUMMARY OF THE INVENTION

Described herein are systems and methods for the transmission of torque and translation of movement in the context of torque. Exemplary embodiments of torque shafts and systems and methods making use of those shafts are described, as well as others.

DETAILED DESCRIPTION OF THE INVENTION

Torque shafts are described herein. The torque shafts are both flexible and capable of transmitting torque. The torque shafts are useful for procedures that require torque and pushability to drive or deploy a device in any application, such as a medical application constituting use in a patient's body. The flexibility and pushability of the torque shafts enable them to curve along passageways in the body, and the torque transferring capability of the shafts enable them to transmit torque in the body to drive or deploy a device in the body. The torque shafts are particularly useful for the deployment of prosthetic heart valves in a patient's heart, which are described in greater detail in application Ser. No. 11/066,126, titled "Prosthetic Heart Valves, Scaffolding Structures, and Systems and Methods for Implantation of Same," filed on Sep. 15, 2005, the entire specification of which is incorporated by reference. Also described herein is a pull-pull torque drive as an alternative to the torque shafts.

Figure 1A:
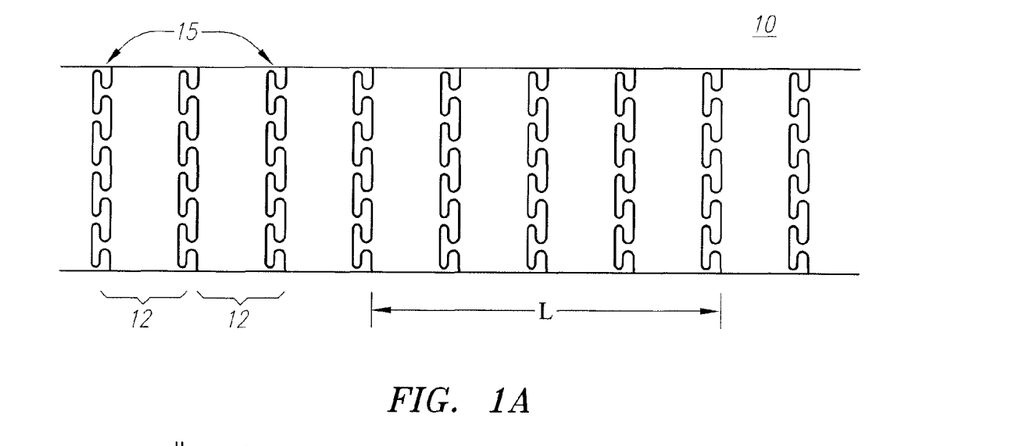
FIGS. 1A-1C show a torque shaft with T-shaped interlocking features according to an embodiment.
Figure 1B:
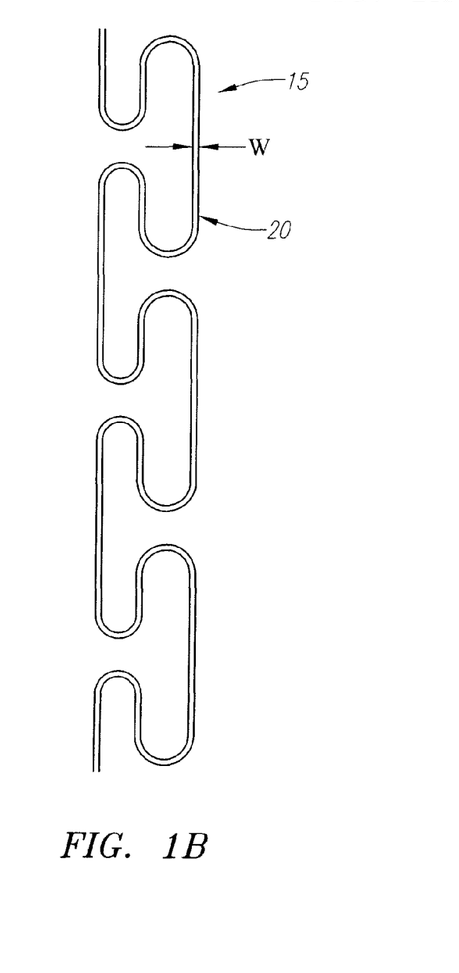
Figure 1C:
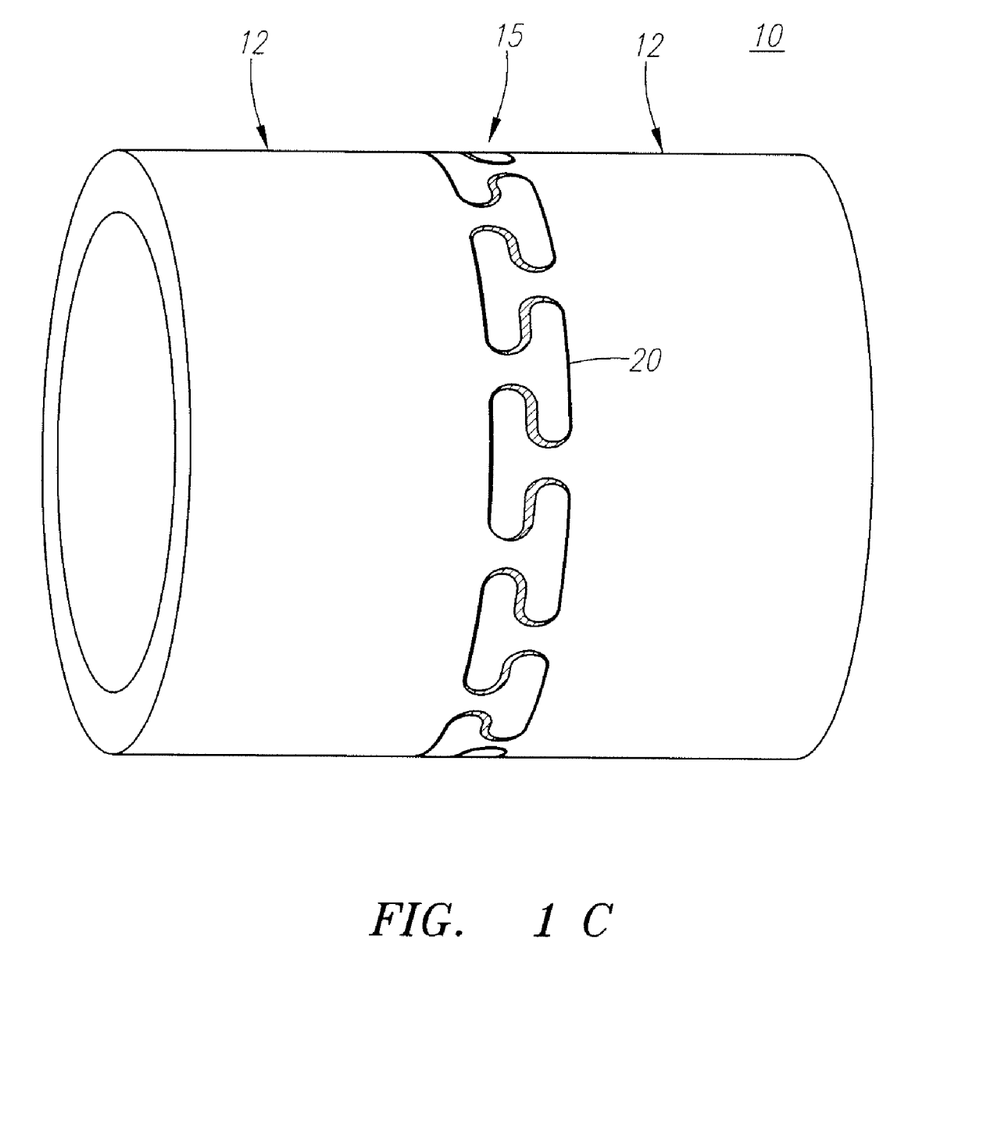
Figure 2A:
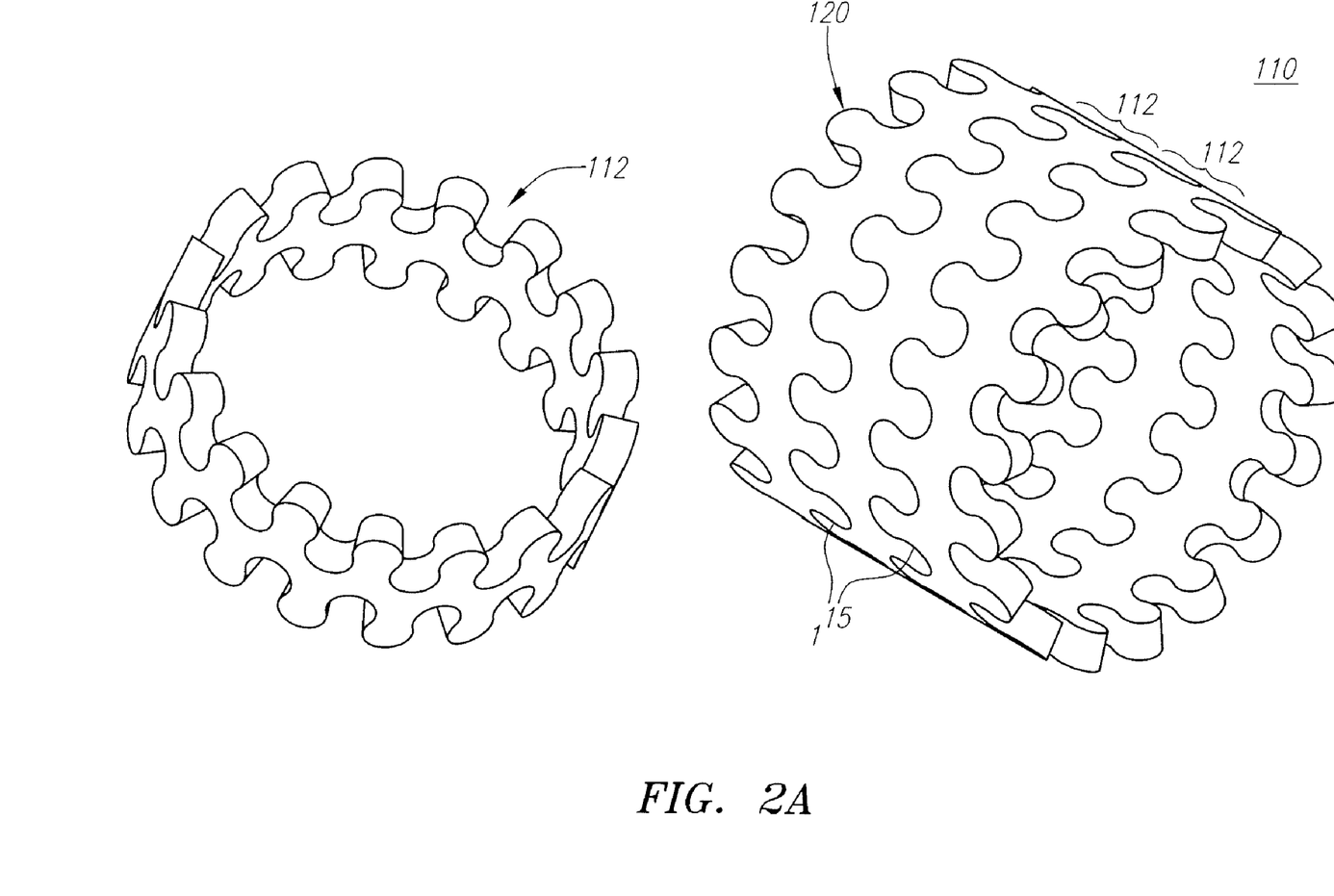
FIGS. 2A-2B show a torque shaft with teardrop shaped interlocking features according to another embodiment.
Figure 2B:
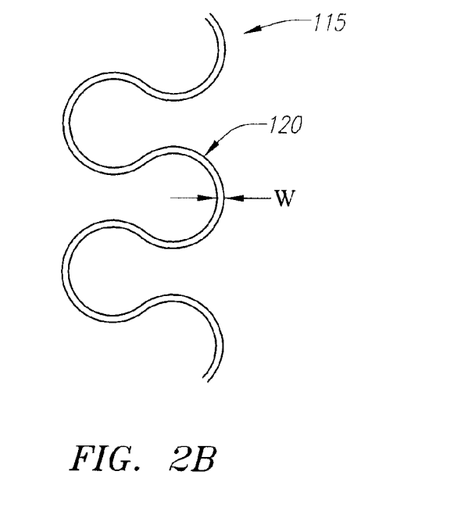

FIGS. 1A-1C show a torque shaft 10 according to an embodiment of the invention. The torque shaft 10 comprises a plurality of interlocking sections 12 cut into a steel tube. The sections 12 are linked together by interlocking geometry of slots 15. Each interlocking slot 15 extends around the circumference of the tube and comprises a plurality of interlocking features 20. The interlocking features 20 of each slot 15 connect two adjacent sections 12 on opposite sides of the slot 15. FIG. 1B shows an expanded view of one of the slots 15 and FIG. 1C shows an expanded perspective view of one of the slots 15. In this embodiment, each slot comprises T-shaped interlocking features 20. FIGS. 2A-2B show a torque shaft 110 according to another embodiment, in which each slot 115 comprises teardrop-shaped interlocking features 120. The geometry of the interlocking features can be any shape that interlocks.

In the preferred embodiment, the torque shaft is fabricated by laser cutting the slots into a steel tube. This may be done by moving the steel tube across a stationary laser under computer control to precisely cut the slots. Laser cutting is well known in the art for fabricating, e.g., stents.

Turning to FIGS. 1B and 2B, each slot 15,115 has a width W defined by the width of the laser cut. The slot width W creates space between adjacent sections that allow adjacent sections 12,112 to move slightly relative to each other. This movement allows adjacent sections 12,112 to bend at a slight angle (e.g., 1-2 degrees) relative to each other. The larger the slot width W, the more adjacent sections 12,112 can bend relative to each other.

The flexibility of the shaft 10,110 per unit length L depends on the amount that adjacent sections 12,112 can bend relative to each other and the number of slots 15,115 per unit length L. Since the amount that adjacent sections 12,112 can bend is determined by the slot width W, the flexibility of the shaft 10,110 per unit length is determined by the slot width W and the number of slots 15,115 per unit length L. The flexibility of the shaft 10,110 is approximately independent of the shape of the interconnecting features of the slots.

Figure 3:
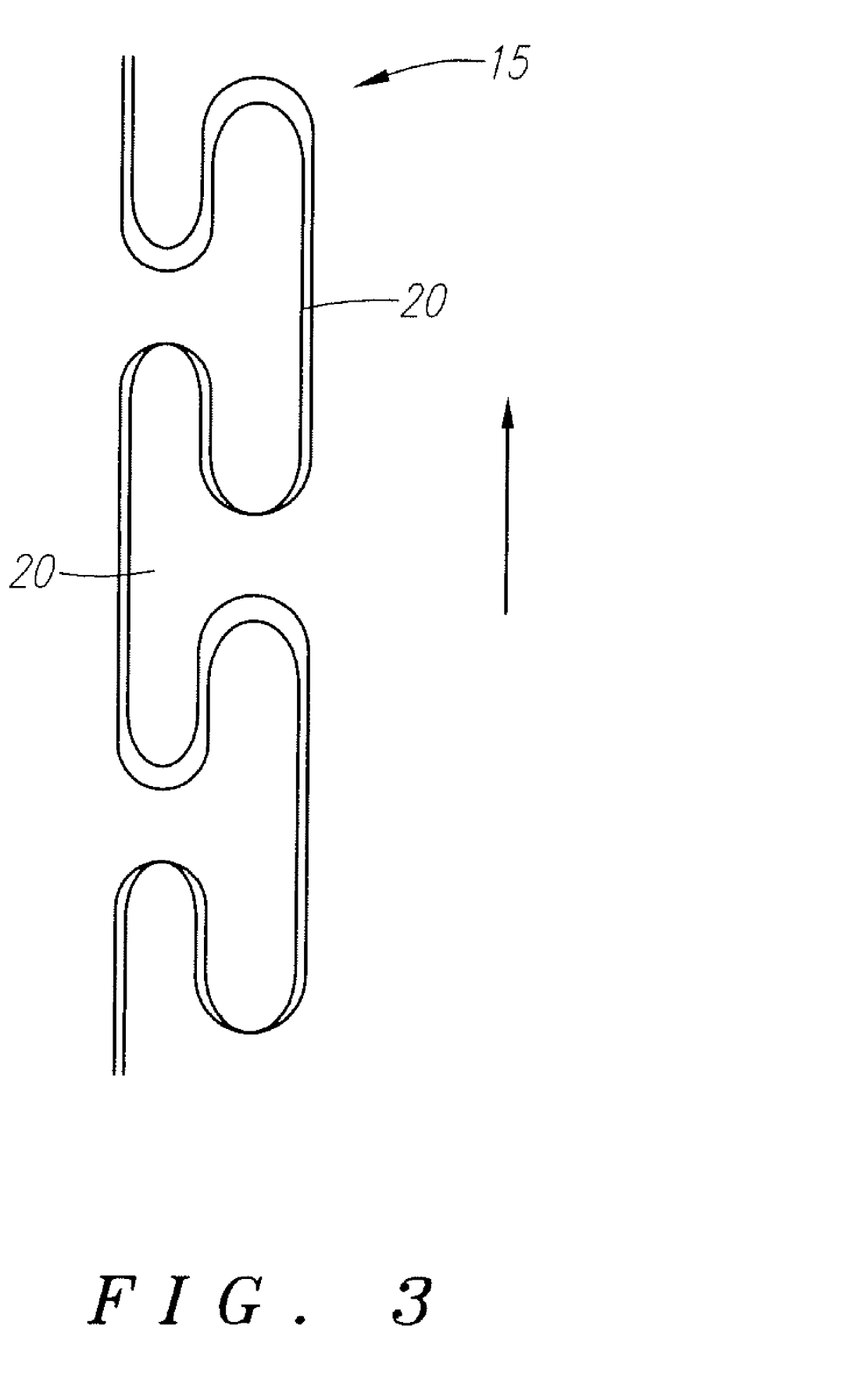
FIG. 3 illustrates the torque transferring capability of the torque shaft.

The interlocking slots 15,115 allow the shaft 10,110 to be flexible while enabling the shaft 10,110 to transmit torque applied at one end of the shaft to the other end of the shaft. The torque transferring capability of the shaft 10 is illustrated in FIG. 3, which shows an expanded view of two adjacent interlocking features 20 of a slot 15. As the shaft 10 is rotated about it longitudinal axis in the direction indicated by the arrow, the adjacent interlocking features 10 of the slot 15 engage each other, at which point torque is transferred between the adjacent sections 12 of the slot 15.

Figure 4:
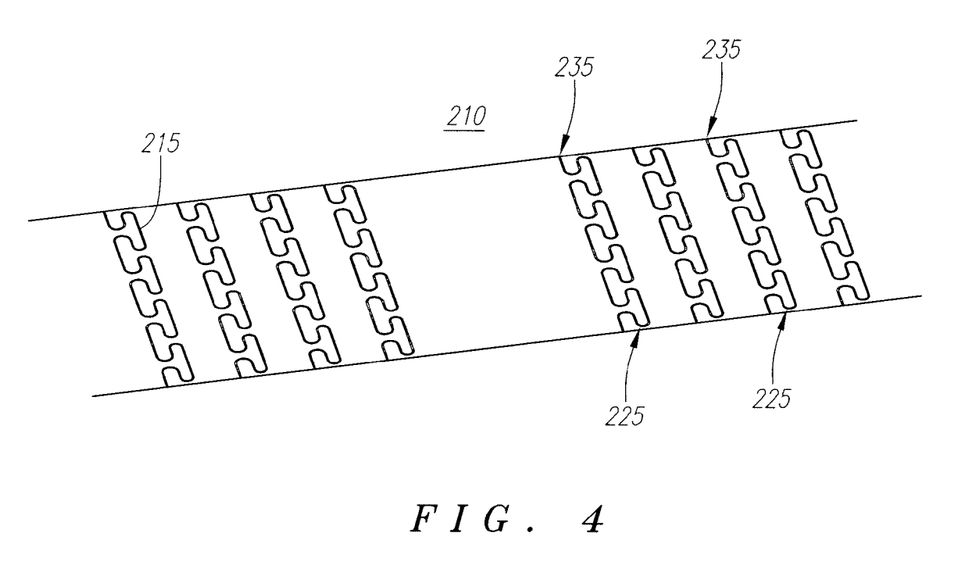
FIG. 4 shows a torque shaft with spiral slots running the length of the torque shaft.

FIG. 4 shows an interlocking slot 215 according to another embodiment. In this embodiment, instead of a plurality of separate interlocking slots along the shaft, a continuous spiral or helical slot 215 runs along the length of the shaft 210. Alternatively, two or more helical slots may run along the length of the shaft. FIG. 4 also shows an example in which two contiguous interspaced helical slots 225 and 235 run along the length of the shaft 210 next to each other. The helical slots may have the same interlocking geometry or different interlocking geometries.

Figure 5:
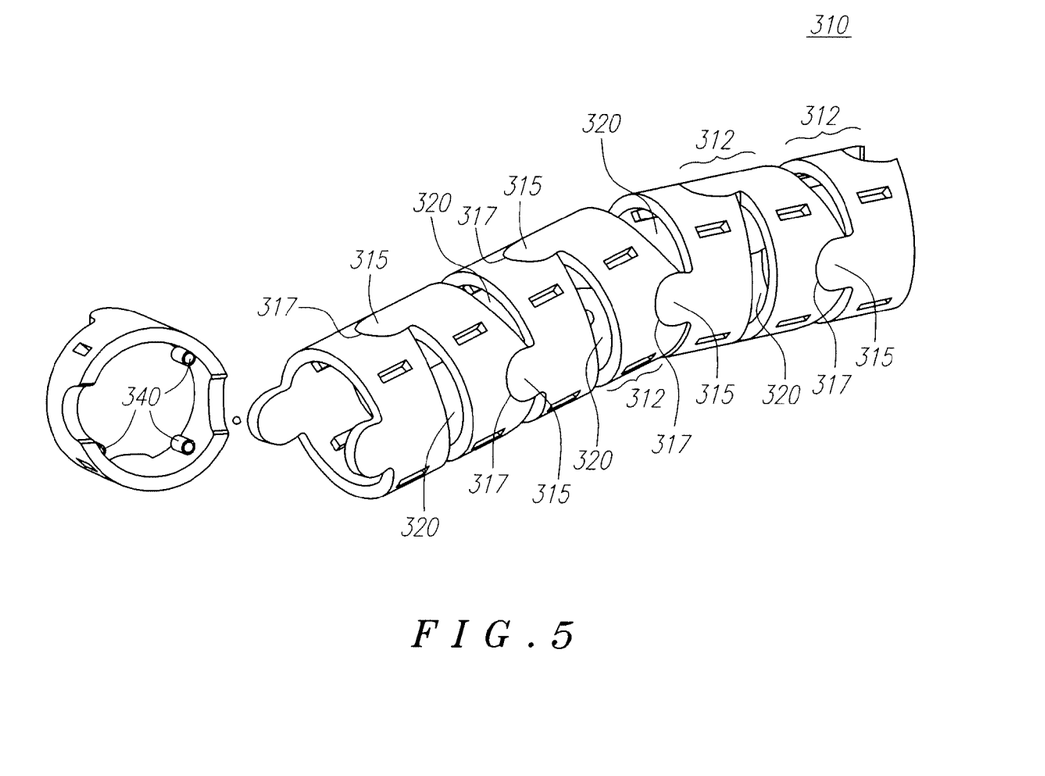
FIGS. 5-6 show a spot-link torque shaft according to another embodiment.
Figure 6:
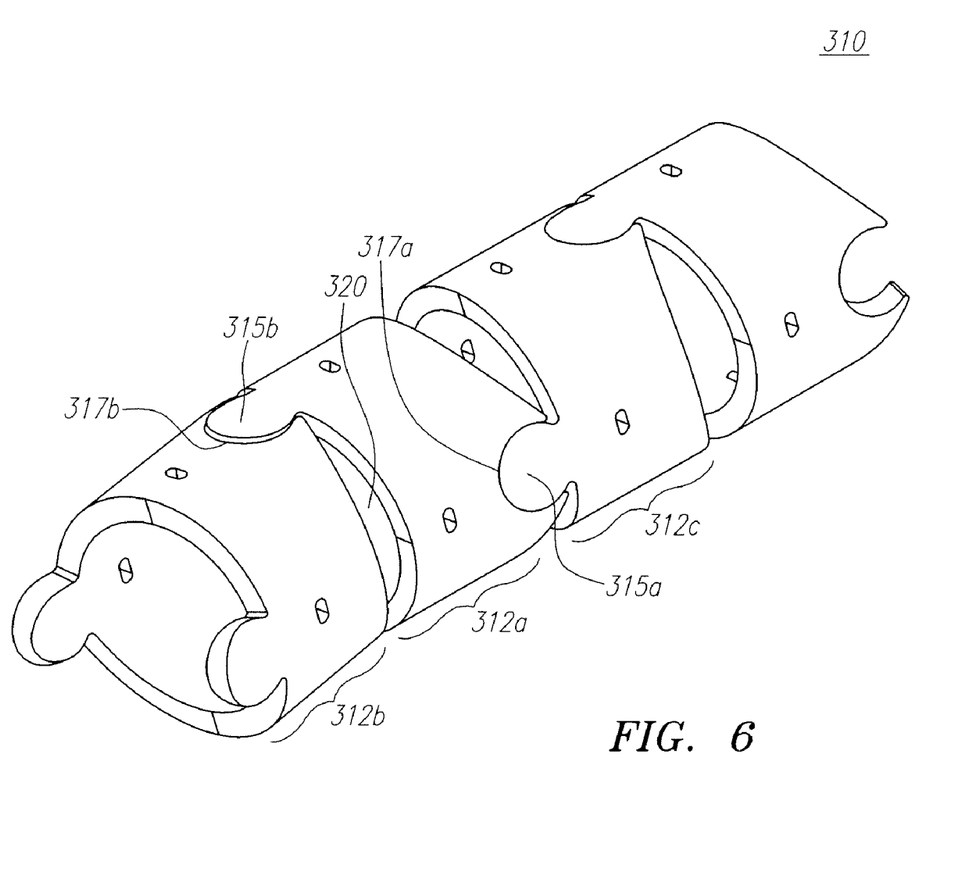

FIGS. 5-6 show a spot-link torque shaft 310 according to another embodiment of the invention. The torque shaft 310 comprises a plurality of interlocking sections 312. Each section 312 comprises two male interlocking features 315 on opposite sides of the section, and two female interlocking features 317 on opposite sides of the section and orientated 90 degrees with respect to the male interlocking features 315. The male interlocking features 315 have circular shapes and the female interlocking features 317 have corresponding inwardly curved shapes for receiving the male interlocking features 315 therein. The male interlocking features 315 of each section 312 fit into the female interlocking features 317 of an adjacent section 312. This fit enables adjacent sections 312 to pivot relative to each other about an axis. Each female interlocking feature 317 curves around the corresponding male interlocking feature 315 more than 180 degrees to prevent adjacent sections 312 from being pulled apart.

To provide space for adjacent sections 312 to pivot, portions of the tube forming the shaft are removed or cut away between the adjacent sections. In this embodiment, wedge-shaped portions of the tube are cut away between adjacent sections to provide pivot spaces 320. The pivot spaces 320 between adjacent sections allow adjacent sections 312 to pivot, e.g., 0-15 degrees, relative to each other.

The male interlocking features 315 of adjacent sections 312 are orientated at 90 degrees from each other. This is done to enable the interlocking features to hold the sections together. This is also done so that the pivot axes of the sections alternate 312 between two perpendicular axes. For example, in FIG. 6, the pivot axis of adjacent sections 312a and 312b is perpendicular to the pivot axis of adjacent sections 312a and 312c. The alternating pivot axes allow the torque shaft 310 to flex or bend in unlimited directions about the axis.

The male interlocking features 315 also enable the torque shaft 310 to transmit torque from one end of the shaft to the other end of the shaft. Each pair of male interlocking features 315 transmits torque between the corresponding adjacent sections 312 when the shaft is rotated along its longitudinal axis. In addition, the interlocking features 315 also provide column strength (compressive) and tensile strength to the shaft 310.

The torque shaft may include optional guides for steering cables. FIG. 5 shows an example in which the torque shaft 310 comprises four equally spaced guides 340 along its inner surface for receiving four steering cables. The guides may also be on the outer surface of the torque shaft.

The spot-link torque shaft has several advantages over the torque shaft with interlocking slots. One advantage is that adjacent sections of the spot-link torque shaft are able to pivot or bend to a much greater degree than adjacent sections of the torque shaft with interlocking slots. As a result, the spot-link torque shaft requires far fewer sections per unit length to flex or bend a given amount per unit length than the torque shaft with interlocking slots. This reduction in the number of sections reduces the amount of laser cutting required to fabricate the spot-link torque shaft compared to the torque shaft with interlocking slots.

Another advantage is that the spot-link torque shaft requires less rotation of the shaft before torque is transmitted from one end of the shaft to the other end of the shaft. Before torque can be transmitted from one end of a torque shaft to the other end, the rotational slack between each one of the adjacent sections of the shaft must be removed by rotating the shaft. Because the spot-link torque shaft has fewer sections than the torque shaft with interlocking slots, the spot-link torque shaft has less rotational slack that needs to be removed before toque is transmitted from one end of the shaft to the other end.

Figure 7:
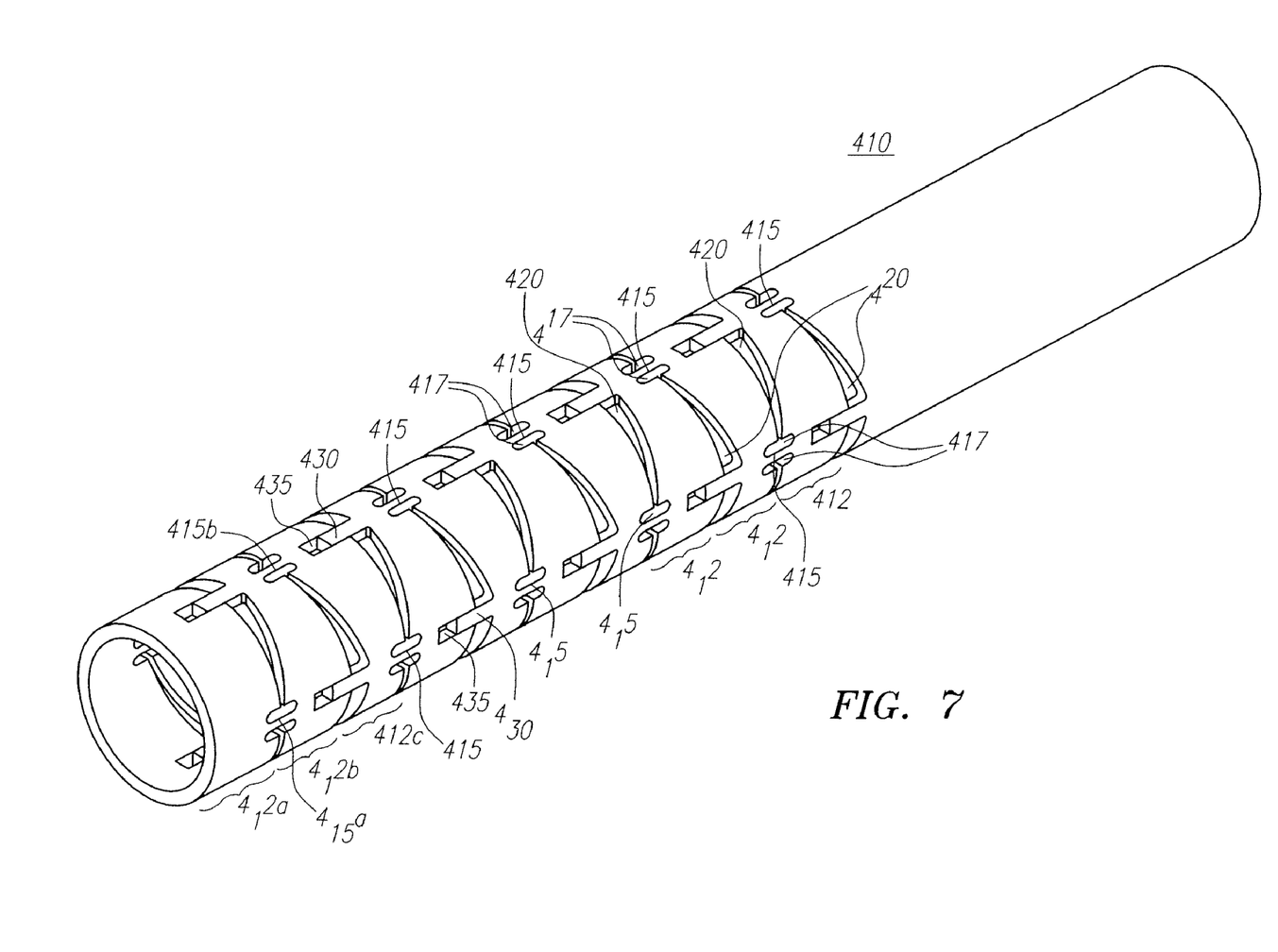
FIG. 7 shows a torque shaft with living hinges according to another embodiment.

FIG. 7 shows a torque shaft 410 according to another embodiment. The torque shaft 410 comprises a plurality of sections 412 connected together by living hinges 415. Adjacent sections 412 are connected to each other by a pair of living hinges 415 on opposite sides of the shaft 410. The sections 412 are laser cut into a tube, in which thin portions of the tube are left connected between the sections 412 to form the living hinges 415. Preferably, the tube is made of a pliable metal, e.g., steel or Nitinol, or other pliable material that enables the living hinges to flex or bend without breaking. Slots 417 are cut on both side of each living hinge 415 to increase the length of the hinge 415 and hence the amount that each hinge can bend. The living hinges 415 enable adjacent sections 412 to flex or bend relative to each other. To provide space for adjacent section 412 to bend, portions of the tube are removed or cut away between adjacent sections. In this embodiment, wedge-shaped portions of the tube are cut away between adjacent sections to provide space 420 to flex.

Adjacent pairs of living hinges 415 are orientated at 90 degrees from each other. For example, in FIG. 7, the pair of living hinges 415a between adjacent sections 412a and 412b are orientated at 90 degrees from the pair of living hinges 415b between adjacent sections 412b and 412c. The 90 degree orientation between adjacent pairs of living hinges 415 enable the torque shaft 410 to flex or bend in more directions.

The torque shaft further comprises a pair of torque keys 430 between adjacent sections 412. Each pair of torque keys 430 extend from opposite sides of a section 412 and is received in a pair of slots 435 in an adjacent section 412. To allow adjacent sections 412 to bend about the hinges 415, the slots 435 are dimensioned so that the corresponding torque keys 430 can slide in the slots 435 to allow bending. The torque keys 430 transmit torque between adjacent sections 412 of the shaft when the shaft is rotated about its longitudinal axis by pushing against the side walls of the corresponding slots 435. The torque keys 430 may be contiguous with the sections 412 or may be made of separate pieces attached to the sections 412.

Figure 8:
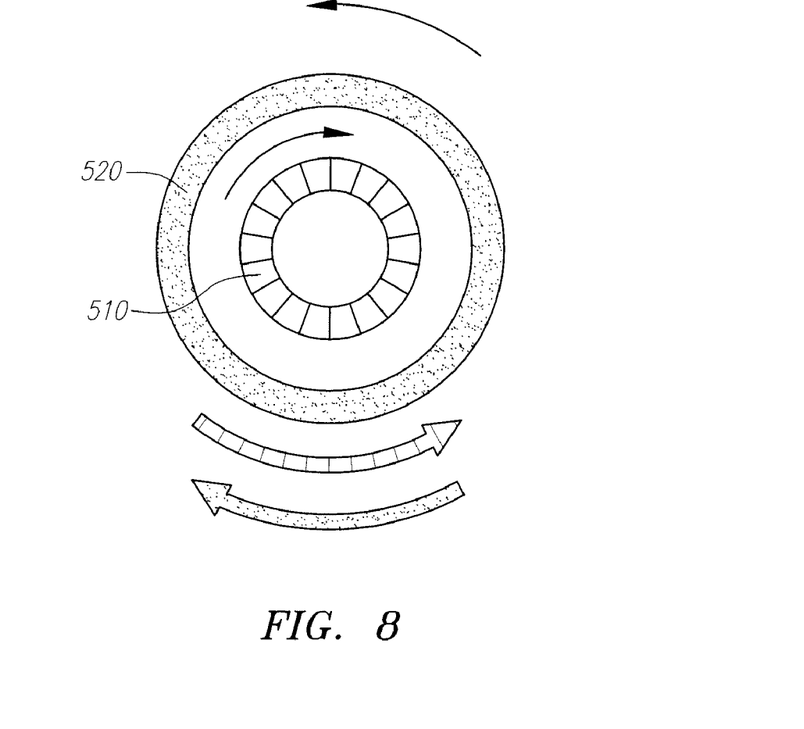
FIGS. 8-9 show two opposing torque shafts according to another embodiment.
Figure 9:
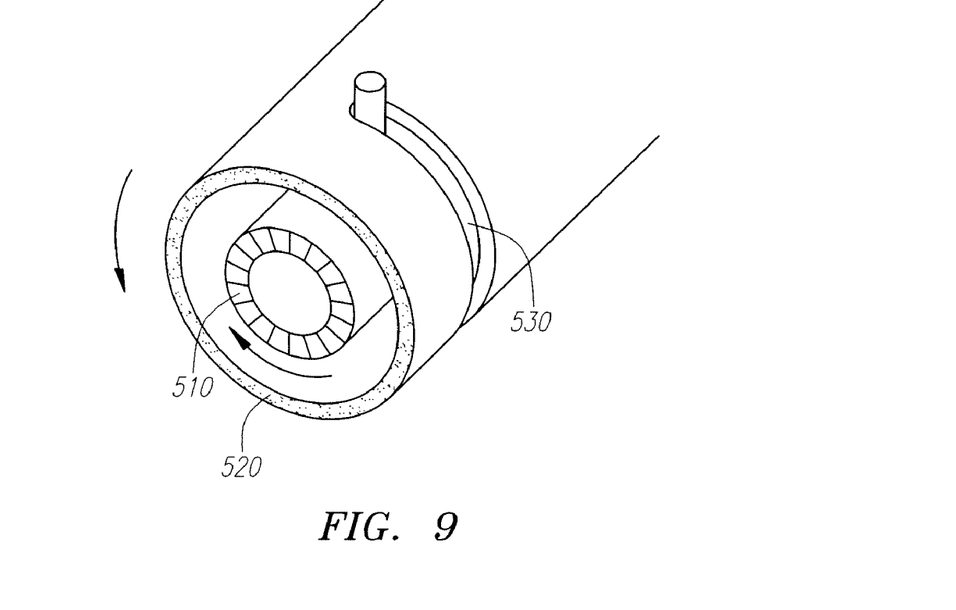

FIGS. 8-9 show two opposing torque shafts 510 and 520 with one of the torque shafts 510 within the other torque shaft 520. As explained above, a torque shaft has to be rotated by a certain amount at one end before torque is transmitted to the other end of the shaft. This amount of rotation is referred to as wind-up.

Since the two torque shafts 510 and 520 oppose each other in rotational direction, each torque shaft can be pre-wound or pre-loaded to remove wind-up before use. In FIG. 8, the outer torque shaft 520 is pre-wound in the counter clockwise direction and the inner torque shaft 510 is pre-wound in the clockwise direction as indicated by arrows. The torque shafts 510 and 520 are pre-wound until the wind-up is removed from each shaft 510 and 520. When the torque shafts 510 and 520 are pre-wound, the outer torque shaft 520 wants to unravel in the clockwise direction and the inner torque shaft 510 wants to unravel in the counter clockwise direction. To prevent the torque shafts 510 and 520 from unravel after they are pre-wound, an interlocking feature can be placed between the two torque shafts.

FIG. 9 shows an example of a pin 525 connected to the inner torque shaft 510 and received in a slot in the outer torque shaft 520. The pin 525 engages an end surface of slot 530, which prevents the two torque shafts 510 and 520 from unraveling. The slot 530 runs along part of the circumference of the outer shaft 520 to allow the ends of the torque shafts 510 and 520 to be rotated in opposing direction.

Figure 10:
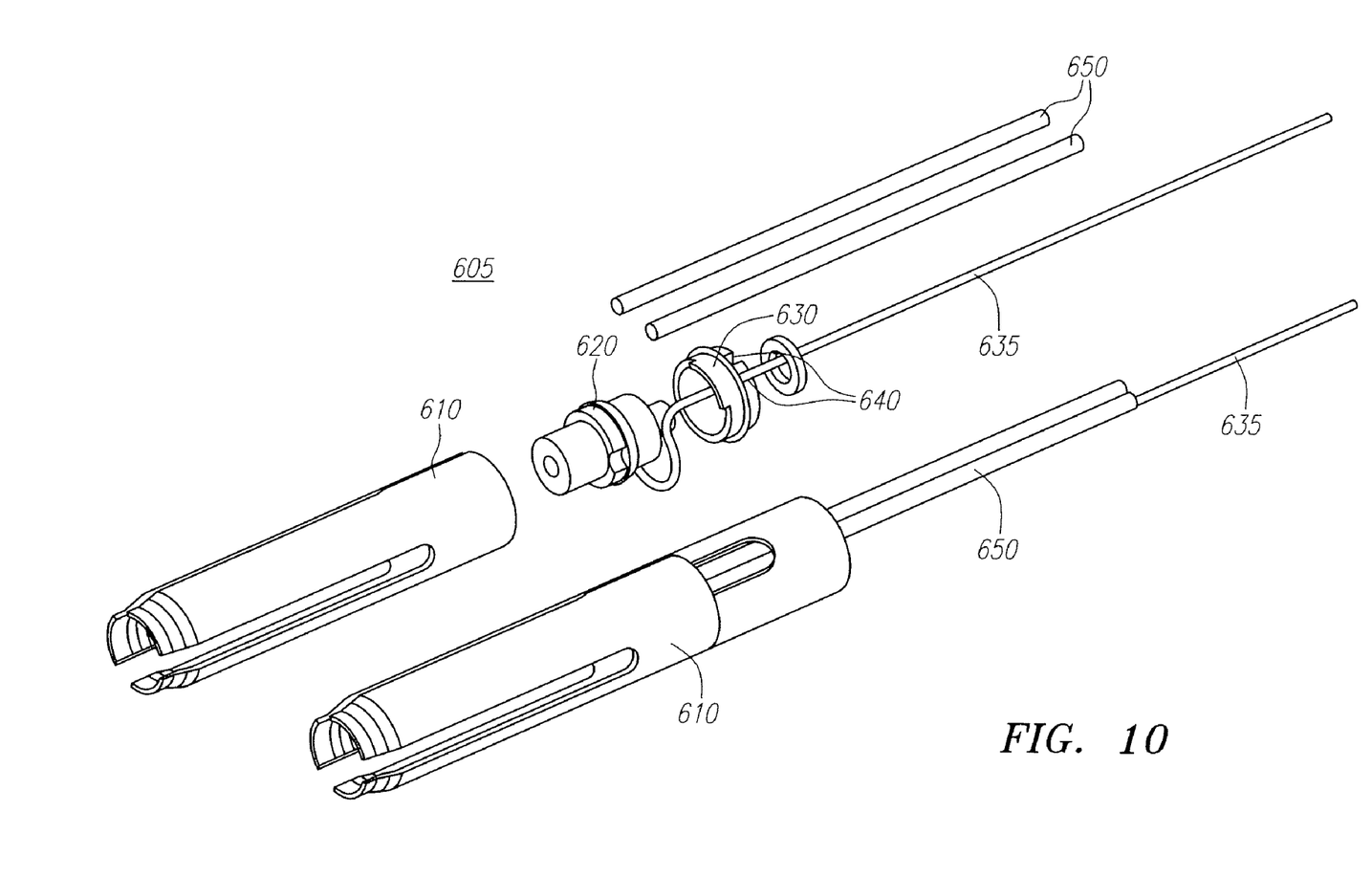
FIG. 10 shows a pull-pull torque drive according to another embodiment.

FIG. 10 shows an exploded and a perspective view of a pull-pull torque drive 605 according to an embodiment. The torque drive 605 comprises a slotted tube 610, a cable drum hub 620, and a sheave 630. The drum hub 620 is placed in the tube 610 and rotates on the sheave 630. The torque drive 605 further comprises two cables 635 running through coil pipes 650 (only one of the cables is shown in FIG. 10). The cables 635 are threaded through channels 640 in the sheave 630 and wound around the drum hub 620 in different directions. The end of each cable 635 is attached to the drum hub 620. FIG. 10 shows one of the cables 635 wound around the hub 620 in one direction. The other cable (not shown) is wound around the hub 620 in the opposite direction.

The cables 635 enable the cable drum hub 620 to be rotated in either direction with respect to the tube 610 by pulling one of the cables 635 axially. Pulling on one of the cables 635 causes that cable 635 to unwind around the hub 620 thereby rotating the hub 620. This also causes the other cable 635 to wind around the hub 620 so that the hub 620 can be rotated in the other direction by pulling the other cable 635.

The pull-pull torque drive 605 is useful for deploying a prosthetic heart valve in a patient, which is described in more detail in application Ser. No. 11/066,126, filed on Sep. 15, 2005.

Figure 11:
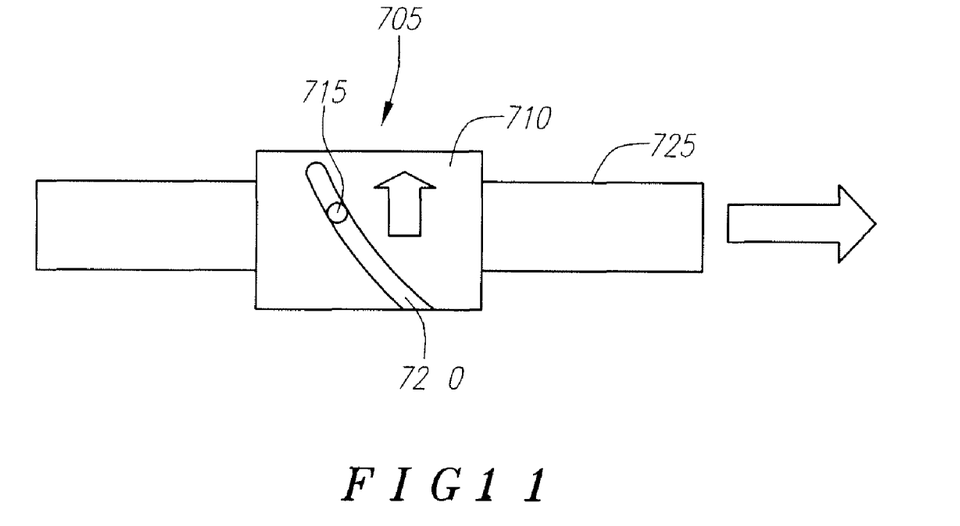
FIG. 11 shows a device for translating axial force applied to the shaft into rotational movement of the shaft.

FIG. 11 shows a device 705 for translating axial movement of the shaft 725 into rotational movement of the shaft 710. This may be used for transmitting torque to the distal end of the shaft by applying axial force to the proximal end of the shaft. The device 705 comprises a cylindrical sleeve 710 with a curved slot 720 and a pin 715 connected to the shaft 725 that slides in the slot 720. When axial force is applied to the shaft 725, the pin 715 connected to the shaft travels along the curved slot 720 of the sleeve 710 causing the sleeve 710 to rotate.

Although the present invention has been described in terms of the presently preferred embodiments, it is to be understood that the disclosure is not to be interpreted as limiting. Various alterations and modifications will no doubt become apparent to those skilled in the art after having read this disclosure.

What is claimed is:

1. An elongate tubular shaft for the transmission of torque, the shaft having a first end and a second end and comprising:
   a plurality of segments coupled along a length of the shaft, wherein a living hinge couples a first segment of the plurality to a second, adjacent segment of the plurality, the living hinge configured to flex to allow the first section to pivot into a space between the first and second sections; and
   an elongate strut extending from the first section and configured to slide within a slot in the second section when the first section pivots, wherein, when the strut is within the slot, a rotation of the shaft causes the strut to transmit torque from the first section to the second section,
   wherein the living hinge is a first living hinge, and wherein the second segment of the plurality is coupled to a third, adjacent segment of the plurality with a second living hinge, the second living hinge configured to flex to allow the second section to pivot into a space between the second and third sections, the first living hinge being at a position on the tubular shaft 90 degrees from the second living hinge.

2. The elongate tubular shaft of claim 1, wherein the elongate strut is a first elongate strut and the slot is a first slot, the shaft further comprising a second elongate strut extending from the second section and configured to slide within a second slot in the third section when the first section pivots, wherein the second elongate strut, when within the second slot, is configured to allow torque transmission from the first section to the second section, and wherein the second elongate strut is at a position on the tubular shaft 90 degrees from the first elongate strut.

* * * * *